US009789079B2

(12) United States Patent
Pan et al.

(10) Patent No.: US 9,789,079 B2
(45) Date of Patent: Oct. 17, 2017

(54) COMPOSITIONS AND METHODS COMPRISING MEDIUM CHAIN TRIGLYCERIDES FOR TREATMENT OF EPILEPSY

(71) Applicant: NESTEC SA, Vevey (CH)

(72) Inventors: Yuanlong Pan, Chesterfield, MO (US); Brian Michael Zanghi, Ballwin, MO (US); Jean-Christophe Bouthegourd, Sannois (FR)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 14/960,559

(22) Filed: Dec. 7, 2015

(65) Prior Publication Data

US 2016/0158183 A1    Jun. 9, 2016

Related U.S. Application Data

(60) Provisional application No. 62/088,797, filed on Dec. 8, 2014.

(51) Int. Cl.

| | |
|---|---|
| *A61K 31/23* | (2006.01) |
| *A61K 9/00* | (2006.01) |
| *A61K 31/515* | (2006.01) |
| *A61K 33/00* | (2006.01) |
| *A61K 31/5377* | (2006.01) |
| *A61K 31/4015* | (2006.01) |
| *A61K 31/5513* | (2006.01) |
| *A61K 31/00* | (2006.01) |
| *A23K 20/158* | (2016.01) |
| *A23K 50/40* | (2016.01) |
| *A23L 33/115* | (2016.01) |
| *A23L 33/12* | (2016.01) |
| *A23L 33/00* | (2016.01) |
| *A23L 33/21* | (2016.01) |
| *A23L 33/125* | (2016.01) |
| *A23K 20/147* | (2016.01) |
| *A23K 20/20* | (2016.01) |
| *A23K 50/42* | (2016.01) |
| *A23K 50/45* | (2016.01) |

(52) U.S. Cl.
CPC ............ *A61K 31/23* (2013.01); *A23K 20/147* (2016.05); *A23K 20/158* (2016.05); *A23K 20/20* (2016.05); *A23K 50/40* (2016.05); *A23K 50/42* (2016.05); *A23K 50/45* (2016.05); *A23L 33/115* (2016.08); *A23L 33/12* (2016.08); *A23L 33/125* (2016.08); *A23L 33/21* (2016.08); *A23L 33/40* (2016.08); *A61K 9/0056* (2013.01); *A61K 31/00* (2013.01); *A61K 31/4015* (2013.01); *A61K 31/515* (2013.01); *A61K 31/5377* (2013.01); *A61K 31/5513* (2013.01); *A61K 33/00* (2013.01); *A23V 2200/00* (2013.01)

(58) Field of Classification Search
CPC ........ A23K 20/158; A23K 50/40; A23L 1/304
USPC ................. 14/221; 514/221, 235.8, 271, 424
See application file for complete search history.

(56) References Cited

U.S. PATENT DOCUMENTS

| | | |
|---|---|---|
| 6,835,750 B1 | 12/2004 | Henderson |
| 7,795,227 B2 | 9/2010 | Kriegler et al. |
| 8,124,589 B2 | 2/2012 | Henderson |
| 8,426,468 B2 | 4/2013 | Henderson |
| 8,445,535 B1 | 5/2013 | Henderson |
| 8,748,400 B2 | 6/2014 | Henderson |
| 9,125,881 B2 | 9/2015 | Henderson |
| 9,603,823 B2 | 3/2017 | Henderson |
| 2006/0128717 A1* | 6/2006 | Sun ...................... C07D 401/04 514/252.03 |
| 2006/0217303 A1 | 9/2006 | Kriegler |
| 2008/0260816 A1 | 10/2008 | Herslof |
| 2010/0292330 A1* | 11/2010 | Pan ....................... A61K 31/198 514/560 |
| 2014/0057885 A1 | 2/2014 | Reddy et al. |

FOREIGN PATENT DOCUMENTS

WO    2014027023 A1    2/2014

OTHER PUBLICATIONS

Sills et al, title: The medium chain triglyceride diet and intractable epilepsy; Arch Dis Child. Dec. 1986; 61(12): p. 1168-1172.*
Musa-Veloso, K et al, "Breath acetone predicts plasma ketone bodies in children with epilepsy on ketogenic diet" Nutrition, Elsevier Inc., US, vol. 22, No. 1, Jan. 1, 2006.
Bechgaard E et al, "Pharmacokinetic and pharmacodynamic response after intranasal administration of diazepan to rabbits", Journal of Pharmacy and Pharmacology, John Wiley & Sons Ltd., vol. 49, No. 8, Jan. 1, 1997.
Piotr Wlaz et al, "Anticonvulsant profile of caprylic acid, a main constituent of the medium chain triglyceride (MCT) ketogenic diet in mice" Neuropharmacology, vol. 62, No. 4, Mar. 1, 2012.
International Search Report and Written Opinion PCT/IB2015/059417, dated Mar. 8, 2016.

* cited by examiner

*Primary Examiner* — Yanzhi Zhang
(74) *Attorney, Agent, or Firm* — Ronald A. Burchett; Julie M Lappin

(57) ABSTRACT

The invention provides compositions and methods for treatment of epilepsy in an animal. In one embodiment, a dietary regime suitable for enhancing the effect of an anti-epileptic drug (AED) in an animal can comprise a food composition comprising a medium chain triglyceride (MCT) and the AED, wherein the MCT is present in the food composition in an effective amount for enhancing the effect of the AED when the food composition and the AED are administered to the animal.

8 Claims, No Drawings

COMPOSITIONS AND METHODS COMPRISING MEDIUM CHAIN TRIGLYCERIDES FOR TREATMENT OF EPILEPSY

CROSS REFERENCE TO RELATED APPLICATIONS

This application claims priority to U.S. Provisional Application Ser. No. 62/088,797 filed Dec. 8, 2014, the disclosure of which is incorporated in its entirety herein by this reference.

BACKGROUND OF THE INVENTION

Field of the Invention

The invention relates generally to compositions and methods for treatment of epilepsy in an animal. Particularly, the present invention relates to the compositions and methods using medium chain triglycerides for the treatment of epilepsy. More particularly, the present invention relates to compositions and methods comprising medium chain triglycerides for enhancing the effect of antiepileptic drugs in animals.

Description of Related Art

Epilepsy is the most common chronic neurological disorder in humans and dogs with an estimated prevalence in dogs of 1-2% in a referral hospital population and 0.6% in first opinion practice. Higher prevalence's up to 18% have been reported in breed specific studies with up to 33% seen in certain families. Further, epilepsy has been associated with increased risk of premature and unexpected death, injuries, cognitive deterioration, neurobehavioral dysfunction and reduced quality of life. Despite on-going research in understanding the pathophysiological manifestation of seizures and epilepsy, the cellular mechanisms remain elusive. As a result, approaches towards epileptic therapy are usually directed towards the control of seizures, most commonly chronic administration of antiepileptic drugs (AEDs), rather than prevention of epileptogenesis or comorbidities. Some of the AEDs routinely used in canine epilepsy include phenobarbital (PB), potassium bromide (KBr), imepitoin, benzodiazepines, gabapentin and levetiracetam. Despite appropriate AED treatment, approximately one third of dogs and humans with idiopathic epilepsy continue to experience difficult to control seizures. Furthermore, AED related side effects such as ataxia, polyphagia, polyuria, polydipsia and incontinence also contribute to reduction in quality of life.

A myriad of anecdotal reports and published literature have suggested the importance of dietary manipulation in seizure management. In particular, the ketogenic diet (KD) has been proposed as an alternative treatment strategy for canine epilepsy. The classic KD consisting of high fat, low protein and low carbohydrate, typically with ratios of up to 4:1 fats to proteins and carbohydrates, was first introduced in the 1920s for use in human childhood epilepsy. The use of KD was initially suggested in order to mimic the metabolic state and biochemical changes associated with fasting, since fasting was proven to possess anticonvulsant properties. A randomized controlled trial in childhood epilepsy showed promising results with 38% and 9%, of the children on KD diet compared to control diet, having greater than 50% and 90% seizure reduction respectively. Current practice in human medicine to use the 'classic' KD diet as a prescription therapy relies on structuring the macronutrient ratio, whereby fat relative to a combined protein and carbohydrates is 4:1. Traditional ketogenic diet has been developed to control drug-resistant (refractory) epilepsy and typically contains 4:1 ratio of fat to protein plus carbohydrates by weight (Kossoff and Rho, ketogenic diets: evidence for short and long-term efficacy. Neurotherapeutics 6:406-414, 2009). In addition, a ketogenic diet with 60% of the calories from MCTs showed anti-epileptic benefits (Huttenlocher et al. Medium-chain triglycerides as a therapy for intractable childhood epilepsy. Neurology 21:1097-1103, 1971). However, such diets have been problematic due to palatability or restrictiveness of certain foods.

Though advances have been made, there remains a need to develop compositions and methods that can treat epilepsy in humans and other animals. Such therapies would be useful to improve the overall quality of life for all involved. For companion animals, these therapies would lead to improved owner satisfaction and would improve the owner-companion animal bond.

SUMMARY OF THE INVENTION

It is, therefore, an object of the present invention to provide compositions and methods useful for treatment of epilepsy in an animal based on our surprising observation that a well-balanced diet with high dietary protein and carbohydrate and a relatively small percent, e.g. 11%, of the calories from medium chain triglycerides (MCTs) are able to enhance the therapeutic efficacy of an existing anti-epileptic drug (AED) in dogs compared with a control diets with similar macronutrient ratios with the exception that all dietary fats come from long chain triglycerides.

In one embodiment, a dietary regime suitable for enhancing the effect of an AED in an animal can comprise a food composition comprising an MCT and the AED. Generally, the MCT is present in the food composition in an effective amount for enhancing the effect of the AED when the food composition and the AED are administered to the animal.

In another embodiment, a method for enhancing the effect of an anti-epileptic drug (AED) in an animal comprising administering a food composition comprising a medium chain triglyceride (MCT) in conjunction with an anti-epileptic drug (AED) to the animal, wherein the MCT is administered in an effective amount for enhancing the effect of the AED in the animal.

In yet another embodiment, a pharmaceutical composition for enhancing the effect of an anti-epileptic drug (AED) in an animal can comprise a medium chain triglyceride (MCT) and the AED. As previously noted, the MCT is generally present in an effective amount for enhancing the effect of the AED when the pharmaceutical composition is administered to the animal.

Other and further objects, features, and advantages of the present invention will be readily apparent to those skilled in the art.

DETAILED DESCRIPTION OF THE INVENTION

Definitions

The following abbreviations may be used herein: MCT(s), medium chain triglyceride(s); AA, arachidonic acid; AED, anti-epileptic drug; ALA, alpha-linolenic acid; ANOVA, analysis of variance; DHA, docosahexaenoic acid; DPA, docosapentaenoic acid; EPA, eicosapentaenoic acid; LA, linoleic acid; LCPUFA, long chain polyunsaturated fatty acids (as used herein LCPUFA refers to one or more such fatty acids); NO, nitric oxide; NORC, nitric oxide releasing compound or compounds; and L-Arg, L-arginine.

The term "animal" means any animal that could benefit from one or more of the methods of the present invention including treatment of epilepsy. Generally, the animal is a human, avian, bovine, canine, equine, feline, hircine, lupine, murine, ovine, and porcine animal. A "companion animal" is any domesticated animal, and includes, without limitation, cats, dogs, rabbits, guinea pigs, ferrets, hamsters, mice, gerbils, horses, cows, goats, sheep, donkeys, pigs, and the like. In one example, the animal can be a human or a companion animal such as a dog or cat.

The term "enhancing the effect of an anti-epileptic drug (AED)" means one or more of increasing the potency or effectiveness of the AED in an animal or preventing, reducing, or delaying epileptic seizures, seizure severity, and/or number of seizures within a cluster of seizures in an animal and/or reducing the efficacious dose or dosing frequency of the AED to an animal. The term "medium chain triglyceride" or "MCT" means any glycerol molecule ester-linked to three fatty acid molecules, each fatty acid molecule having 5-12 carbons. MCTs may be represented by the following general formula (Formula 1):

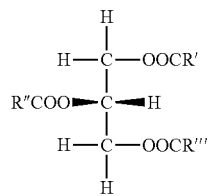

where R', R" and R'" are fatty acids having 5-12 carbons in the carbon backbone esterified to a glycerol backbone. The MCTs of the invention may be prepared by any process known in the art, such as direct esterification, rearrangement, fractionation, transesterification, or the like. For example, the MCTs may be prepared by the rearrangement of a vegetable oil such as coconut oil. The length and distribution of the chain length may vary depending on the source oil. For example, MCTs containing 1-10% C6, 30-60% C8, 30-60% C10, 1-10% C12 are commonly derived from palm and coconut oils. MCTs containing greater than about 95% C8 at R', R" and R'" can be made by semi-synthetic esterification of octanoic acid to glycerin. Also useful herein are mixtures comprising MCTs with about 50% total C8 and/or about 50% total C10. Commercial sources for the foregoing MCT compositions are available and known to the skilled artisan. Such MCTs behave similarly and are encompassed within the term MCTs as used herein.

The term "long chain polyunsaturated fatty acids" or "LCPUFA" means any one or more monocarboxylic acids having at least 20 carbon atoms and at least two double bonds. Examples of LCPUFA include (n-6) fatty acids, such as arachidonic acid (AA), and (n-3) fatty acids, such as eicosapentaenoic acid (EPA), docosapentaenoic acid (DPA) and docosahexaenoic acid (DHA).

The term "fish oil" means a fatty or oily extract, relatively rich in LCPUFA, whether crude or purified, obtained from a sea animal, e.g. a cold-water fish such as, but not limited to, salmon, tuna, mackerel, herring, sea bass, striped bass, halibut, catfish, and sardines, as well as shark, shrimp, and clams, or any combination thereof. Fish oil is generally a term of art used by ingredient suppliers and encompasses a range or products of varying PUFA content and purity.

The term "nitric oxide releasing compounds" or "NORC" means any compound or compounds that cause or can result in the release of nitric oxide in an animal. Examples of such compounds include L-arginine, L-arginine-containing peptides and proteins, and analogs or derivatives thereof that are known or determined to release nitric oxide, such as arginine alpha-ketoglutarate, GEA 3175, sodium nitroprusside, glyceryl trinitrate, S-nitroso-N-acetyl-penicillamine, nitroglycerin, S—NO-glutathione, NO-conjugated non-steroidal anti-inflammatory drugs (e.g., NO-naproxen, NO-aspirin, NO-ibuprofen, NO-Diclofenac, NO-Flurbiprofen, and NO-Ketoprofen), NO-releasing compound-7, NO-releasing compound-5, NO-releasing compound-12, NO-releasing compound-18, diazenium diolates and derivatives thereof, diethylamine NONOate, and any organic or inorganic compound, biomolecule, or analog, homolog, conjugate, or derivative thereof that causes the release of nitric oxide, particularly "free" NO, in an animal.

The term "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In one embodiment, the particular disease, condition, or disorder can be epilepsy.

The dosages expressed herein are in milligrams per kilogram of body weight per day (mg/kg/day) unless expressed otherwise.

The term "aging" means being of advanced age such that the animal has exceeded 50% of the average lifespan for its particular species and/or breed within a species. For example, if the average lifespan for a given breed of dog is 10 years, then a dog within that breed greater than 5 years old would be considered "aging" for purposes herein. "Healthy aging animals" are those with no known diseases, particularly diseases relating to epilepsy such as might confound the results. In studies using healthy aging animals, cohort animals can be also healthy aging animals, although other healthy animals with suitable cognitive, motor, or behavioral functioning may be suitable for use as comparative specimens.

The term "food" or "food product" or "food composition" means a product or composition that is intended for ingestion by an animal, including a human, and provides nutrition to the animal.

As used herein, a "food product formulated for human consumption" is any composition specifically intended for ingestion by a human being. The term "pet food" or "pet food composition" means a composition intended for consumption by animals, in one aspect, by companion animals. A "complete and nutritionally balanced pet food" is one that contains all known required nutrients for the intended recipient or consumer of the food, in appropriate amounts and proportions, based for example on recommendations of recognized authorities in the field of companion animal nutrition. Such foods are therefore capable of serving as a sole source of dietary intake to maintain life or promote production, without the addition of supplemental nutritional sources. Nutritionally balanced pet food compositions are widely known and used in the art. The term includes any food, feed, snack, food supplement, treat, meal substitute, or meal replacement, whether intended for a human or another animal. Animal food includes food or feed intended for any domesticated or wild species. In some embodiments, a food for an animal represents a nutritionally complete food composition, e.g., a pelleted, extruded, or dry food. Examples of such animal foods include extruded pet foods, such as foods for dogs and cats.

The term "dietary supplement" means a product that is intended to be ingested in addition to the normal animal diet. Dietary supplements may be in any form, e.g., solid, liquid, gel, tablets, capsules, powder, and the like. In one aspect, they can be provided in convenient dosage forms. In some embodiments, they can be provided in bulk consumer packages such as bulk powders, liquids, gels, or oils. In other embodiments, supplements can be provided in bulk quantities to be included in other food items such as snacks, treats, supplement bars, beverages and the like.

The term "dietary regime" refers to a combination of compositions that can be administered to an animal to enhance the effect of an anti-epileptic drug (AED). Generally, the compositions include an MCT and an AED and can be administered separately, as a combination, or as a single composition.

The term "long-term administration" means periods of repeated administration or consumption in excess of one month. Periods of longer than two, three, or four months can be used for certain embodiments. Also, more extended periods can be used that include longer than 5, 6, 7, 8, 9, or 10 months. Periods in excess of 11 months or 1 year can also be used. Longer term use extending over 1, 2, 3, or more years are included in the invention. For certain aging animals, the animal will continue consuming on a regular basis for the remainder of its life. This can also be referred to as consumption for "extended" periods.

The term "regular basis" means at least monthly dosing with the compositions or consumption of the compositions, and in one aspect, means at least weekly dosing. More frequent dosing or consumption, such as twice or three times weekly, can be performed in certain embodiments. Still, in other embodiments, regimens can be used that comprise at least once daily consumption. The skilled artisan will appreciate that the blood level of a compound or certain metabolites of that compound or which result after the consumption of that compound, may be a useful tool for assessing or determining dosing frequency. For example, for determining dosage or dosage frequency for compositions comprising MCTs or AEDs, the blood concentration of ketone bodies, a specific ketone body, an AED, or a metabolite of AED, may provide useful information. A frequency, regardless of whether expressly exemplified herein, that allows maintenance of a desired blood level of the measured compound, such as a ketone body or AED, within acceptable ranges can be useful herein. The skilled artisan will appreciate that dosing frequency will be a function of the composition that is being consumed or administered, and some compositions may require more or less frequent administration to maintain a desired blood level of the measured compound (e.g., a ketone body or AED).

The term "oral administration" or "orally administering" means that the animal ingests, or a human is directed to feed, or does feed, the animal one or more of the compositions described herein. Wherein a human is directed to feed the composition, such direction may be that which instructs and/or informs the human that use of the composition may and/or will provide the referenced benefit, for example, reducing seizures. Such direction may be oral direction (e.g., through oral instruction from, for example, a physician, veterinarian, or other health professional, or radio or television media (i.e., advertisement), or written direction (e.g., through written direction from, for example, a physician, veterinarian, or other health professional (e.g., prescriptions), sales professional or organization (e.g., through, for example, marketing brochures, pamphlets, or other instructive paraphernalia), written media (e.g., internet, electronic mail, website, or other computer-related media), and/or packaging associated with the composition (e.g., a label present on a container holding the composition), or a combination thereof (e.g., label or package insert with directions to access a website for more information).

The term "in conjunction" means that an MCT, an AED, or other compound or composition of the present invention are administered to an animal (1) together in a food composition or (2) separately at the same or different frequency using the same or different administration routes at about the same time or periodically. "Periodically" means that the agent is administered on a dosage schedule acceptable for a specific agent and that the food is fed to an animal routinely as appropriate for the particular animal. "About the same time" generally means that the food and agent are administered at the same time or within about 72 hours of each other. "In conjunction" specifically includes administration schemes wherein an AED is administered for a prescribed period and the composition comprising the MCT is administered indefinitely.

The term "individual" when referring to an animal means an individual animal of any species or kind.

The term "microorganism" encompasses at least bacteria, molds and other fungi, and yeasts. Probiotics are beneficial microorganisms that can survive or even multiply and thrive in the gastrointestinal tract of an animal. Probiotics can contribute to the overall health of an animal generally and particularly to the gastrointestinal health of the animal.

The term "single package" means that the components of a kit are physically associated, in or with one or more containers, and considered a unit for manufacture, distribution, sale, or use. Containers include, but are not limited to, bags, boxes or cartons, bottles, packages of any type or design or material, over-wrap, shrink-wrap, affixed components (e.g., stapled, adhered, or the like), or combinations of any of the foregoing. For example, a single package kit may provide containers of individual compositions and/or food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain, for example, instructions on how to use the kit, or safety or technical information about one or more components of a kit. Examples of information that can be provided as part of a virtual kit include instructions for use; safety information such as material safety data sheets; poison control information; information on potential adverse reactions; clinical study results; dietary information such as food composition or caloric composition; general information on cognitive, behavioral, or motor function; diseases that affect cognitive, behavioral, or motor function, such as epilepsy; treating cognitive, behavioral, or motor function; treating epilepsy; or general information on treatment or preservation of cognitive, behavioral, or motor function; caregiver information for those caring for animals with cognitive, behavioral, or motor function challenges such as epilepsy; and use, benefits, and potential side-effects or counter-indications for AEDs.

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used throughout, ranges are used herein in shorthand, so as to avoid having to set out at length and describe each and every value within the range. Any appropriate value within the range can be selected, where appropriate, as the upper value, lower value, or the terminus of the range.

As used herein, embodiments, aspects, and examples using "comprising" language or other open-ended language can be substituted with "consisting essentially of" and "consisting of" embodiments.

As used herein and in the appended claims, the singular form of a word includes the plural, and vice versa, unless the context clearly dictates otherwise. Thus, the references "a", "an", and "the" are generally inclusive of the plurals of the respective terms. For example, reference to "a puppy", "a method", or "a food" includes a plurality of such "puppies", "methods", or "foods". Reference herein, for example to "an MCT" includes a plurality of such MCTs, whereas reference to "pieces" includes a single piece. Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Where used herein the term "examples," particularly when followed by a listing of terms is merely exemplary and illustrative, and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved. Full citations for publications not cited fully within the specification are set forth at the end of the specification.

The Invention

The present inventors have discovered that administration of a medium chain triglyceride (MCT) with an anti-epileptic drug (AED) can provide a synergistic effect for the treatment of epilepsy in an animal. Additionally, the present methods and composition can utilize low proportions of MCTs and high proportions of dietary carbohydrates for dietary management of canine epilepsy, as compared to traditional ketogenic diets. As such, the present epileptic treatments do not require a ketogenic diet, although the use of such diets is not proscribed. Such synergism can be measured against comparable diets not having MCTs. In one embodiment, the present administration results in a reduction in seizure frequency of the animal by at least 50% compared to administration of the AED with a food composition not containing the MCT. In various embodiments, such reduction in seizures can be at least 10%, 20% 30% 40%, 50%, 60% 70%, 80%, 90%, or in one specific aspect, 100%.

As such, in one embodiment, a dietary regime suitable for enhancing the effect of an anti-epileptic drug (AED) in an animal can comprise a food composition comprising a medium chain triglyceride (MCT) and the AED. Generally, the MCT is present in the food composition in an effective amount for enhancing the effect of the AED when the food composition and the AED are administered to the animal.

In another embodiment, a method for enhancing the effect of an anti-epileptic drug (AED) in an animal can comprise administering a food composition comprising a medium chain triglyceride (MCT) in conjunction with an anti-epileptic drug (AED) to the animal, wherein the MCT is administered in an effective amount for enhancing the effect of the AED in the animal.

In yet another embodiment, a pharmaceutical composition for enhancing the effect of an anti-epileptic drug (AED) in an animal can comprise a medium chain triglyceride (MCT) and the AED. As previously noted, the MCT is generally present in an effective amount for enhancing the effect of the AED when the pharmaceutical composition is administered to the animal.

The MCTs can be any MCT suitable for administration to an animal. MCTs can be obtained from any suitable source, synthetic or natural. Examples of natural sources of MCT include plant sources such as coconuts and coconut oil, palm kernels and palm kernel oils, and animal sources such as milk from any of a variety of species. In one embodiment, the MCT can comprise a compound having the structure shown in Formula 1 wherein the R', R", and R''' esterified to the glycerol backbone are each independent fatty acids having 5-12 carbons. In certain embodiments, greater than about 95% of the R', R", and R''' are 8 carbons in length. In one aspect, the remaining R', R", and R''' can be 6-carbon or 10-carbon fatty acids. In other embodiments, greater than at least or about 30, 40, or 50% of R', R", and R''' are C8, and/or greater than at least or about 30, 40, or 50% of R', R", and R''' are C10. In one specific embodiment, about 50% of the R', R", and R''' are C8 and about 50% of R', R", and R''' are C10.

For pet foods and food products formulated for human consumption, the amount of MCTs as a percentage of the composition can be in the range of about 1% to about 15% of the composition, although a lesser or greater percentage can be supplied. In various embodiments, the amount can be about or between any of the following: 1.0%, 1.5%, 2.0%, 2.5%, 3.0%, 3.5%, 4.0%, 4.5%, 5.0%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, or more, of the composition. Dietary supplements may be formulated to contain several fold higher concentrations of MCTs, to be amenable for administration to an animal in the form of a tablet, capsule, liquid concentrate, or other similar dosage form, or to be diluted before administration, such as by dilution in water, spraying or sprinkling onto a pet food, and other similar modes of administration. For a dietary supplement, MCTs alone may be administered directly to the animal or applied directly to the animal's regular food. Dietary supplement formulations in various embodiments contain about 30% to about 100% MCTs, although lesser amounts may also be used.

The AEDs can be any AED suitable for treatment of epilepsy in an animal. Examples of AEDs include, without limitation, acetazolamide, carbamazepine, chlorazepate, clobazam, clonazepam, diazepam, eslicarbazepine acetate, ethisyxunudem, ethosuximide, felbamate, gabapentin, imepitoin, keppra, lacosamide, lamotrigine, levetiracetam, methylphenobarbitone, nitrazepam, oxcarbazepine, perampanel, piracetam, phenobarbital, phenytoin, potassium bromide, pregabalin, primidone, retigabine, rufinamide, sodium bromide, sodium valproate, stiripentol, sulthiame, tiagabine, topiramate, valporic acid, vigabatrin, zonisamide, salts thereof, derivatives thereof, and mixtures thereof.

Generally, the AED can be administered to the animal in any amount that is sufficient for treatment of epilepsy. In one embodiment, the AED can be administered in an amount of about 0.1 mg/kg/day to about 50 mg/kg/day. In one aspect, the AED can be administered in an amount of 20 mg/kg/day to 30 mg/kg/day.

The present food compositions can comprise other ingredients that can be beneficial to cognitive function, such as LCPUFA, NORCs, B vitamins, and antioxidants. The LCPUFA can be any LCPUFA suitable for administration to an animal. LCPUFAs can be obtained from any suitable source, synthetic or natural. Sources of LCPUFA include natural sources of such fatty acids such as, without limitation, primrose; dark green vegetables such as spinach; algae and blue-green algae such as *spirulina*; plant seeds and oils from plants such as flax, canola, soybean, walnut, pumpkin, safflower, sesame, wheat germ, sunflower, corn, and hemp; and fish such as salmon, tuna, mackerel, herring, sea bass, striped bass, halibut, catfish, sardines, shark, shrimp, and clams; and the extracted oils of any one or more of the foregoing. The LCPUFA may also be synthetic, and as such may be produced according to any means suitable in the art, from any suitable starting material. It is to be understood the LCPUFA may comprise a blend of any one or more LCPUFA from any one or more sources, such as those exemplified above, whether natural or synthetic.

The NORCs can be any NORC suitable for administration to an animal. NORCs can be obtained from any suitable source, synthetic or natural. In various embodiments, the NORC comprises arginine. Sources of arginine include, without limitation, animal and plant proteins. Examples of plants considered rich in arginine content and suitable for use herein include, but are not limited to, legumes such as soy, lupins, and carob; grains such as wheat and rice; and fruits such as grapes. Seeds and nuts of plants such as cacao and peanut are also considered rich in arginine content and are therefore useful herein. Some examples of suitable animal proteins considered rich in arginine content are poultry and fish products. The NORC can also be synthetically produced, according to any suitable means in the art. As with LCPUFA, the NORC content of any composition disclosed herein can include a blend of any natural or synthetic NORC. Both LCPUFA and NORC, whether natural or synthetic, can be obtained directly or provided by a commercial source.

The B vitamins can be any B vitamin suitable for administration to an animal. B vitamins include vitamins B1 (thiamine), B2 (riboflavin), B3 (aka P or PP) (niacin, including nicotinic acid and/or nicotinamide), B5 (pantothenic acid), B6 (pyridoxine), B7 (aka H) (biotin), B8 (myo-inositol), B9 (aka M or B-c) (folic acid), B12 (cobalamin), or salts, conjugates, or derivatives thereof recognized of found to have B vitamin activity. Combinations of any of the foregoing are also useful herein and are sometimes referred to herein as "mixtures" of B vitamins. Since the vitamin requirements vary for different species, not all of the listed compounds are deemed vitamins for all species. For example, since it is known that myo-inositol can be synthesized by humans, it is no longer deemed a vitamin, as it is not required for adequate human nutrition.

The antioxidants can be any antioxidant suitable for administration to an animal. Antioxidants are well known in the art, particularly the art of food technology and food formulation. Natural antioxidant compounds include vitamins (such as A, C and E, and derivative, conjugates, or analogs thereof), as well as plant extracts, including extracts from fruit, vegetables, herbs, seeds, and other types and/or parts of plants. Compounds such as α-lipoic acid, chlorophyll and derivatives thereof, glutathione, ubiquinols (e.g., coenzyme Q10), carotenoids (e.g., lycopene), flavonoids, phenolic acids and polyphenols, and pycnogenol are known to be excellent antioxidants. Some examples of plant sources of antioxidants include those from fruits such as berries (cherry, blackberry, strawberry, raspberry, crowberry, blueberry, bilberry/wild blueberry, black currant), pomegranate, grape, orange, plum, pineapple, kiwi fruit, and grapefruit; those from vegetables including kale, chili pepper, red cabbage, peppers, parsley, artichoke, Brussels sprouts, spinach, lemon, ginger, garlic, and red beets; those from dry fruits like apricots, prunes, and dates; from legumes including broad beans, pinto beans, and soybeans. Also nuts and seeds such as pecans, walnuts, hazelnuts, ground nut, and sunflower seeds; cereals such as barley, millet, oats, and corn. Many natural antioxidants are also available from a wide variety of spices including cloves, cinnamon, rosemary, and oregano. Less widely known sources of antioxidants include *Ginkgo biloba*, and tropical plants such as uyaku, and *carica papaya*. Antioxidant properties of various teas and green tea, as well as fermented products such as red wine, have become of great interest in recent years and such would be suitable for use herein. Selenium is an excellent oxygen scavenger and works well, especially with vitamin or related tocopherol compounds. Synthetic dietary antioxidants include butylated hydroxyanisole (BHA) and butylated hydroxytoluene (BHT) which are commonly used in food products. Any of the foregoing, alone or in combination, is suited for use herein, as are combinations of natural and synthetic antioxidants.

LCPUFA, NORC, B vitamins, and antioxidants if included in the composition, can be present in individual amounts for general health or for enhancing cognitive function. In some embodiments, the compositions can individually comprise from about 0.1% to about 50% LCPUFA, from about 0.1% to about 20% NORC, from about 0.1 to 40 times the recommended daily requirement (RDA) of B vitamins, and/or from about 0.1 to 25 times the RDA of antioxidants. In various embodiments, the compositions can comprise from about 1 to about 30% LCPUFA, and in one aspect, from about 1 to about 15% LCPUFA. In other embodiments, the compositions can comprise from about 1 to about 15% NORC, and in one aspect, from about 1 to about 10% NORC. In still other embodiments, the compositions can comprise B vitamins in an amount from about 1 to 20 times the RDA, and in one aspect, from about 4 to 10 times the RDA. In yet other embodiments, the compositions can comprise antioxidants in an amount from about 0.01 to 15 times the RDA, in one aspect, from about 0.01 to 5 times the RDA, and in one specific aspect, from about 0.01 to 2 times the RDA The compositions may further comprise substances such as minerals, other vitamins, salts, functional additives including, for example, palatants, colorants, emulsifiers, antimicrobial or other preservatives. Minerals that may be useful in such compositions include, for example, calcium, phosphorous, potassium, sodium, iron, chloride, boron, copper, zinc, magnesium, manganese, iodine, selenium and the like. Examples of additional vitamins useful herein include such fat soluble vitamins as A, D, E, and K. Inulin, amino acids, enzymes, coenzymes, and the like may be useful to include in various embodiments.

In one embodiment, the food compositions can be formulated as human food compositions or pet food compositions. Such compositions include foods intended to supply the necessary dietary requirements for an animal, animal treats (e.g., biscuits), or dietary supplements. The compositions may be a dry composition (e.g., kibble), semi-moist composition, wet composition, or any mixture thereof. In another embodiment, the composition can be a dietary supplement such as a gravy, drinking water, beverage, yogurt, powder, granule, paste, suspension, chew, morsel, treat, snack, pellet, pill, capsule, tablet, or any other suitable delivery form. The dietary supplement can comprise a high concentration of the MCTs. This permits the supplement to be administered to the animal in small amounts, or in the alternative, can be diluted before administration to an animal. The dietary supplement may require admixing, or can be admixed with water or other diluent prior to administration to the animal.

In one embodiment, the compositions are refrigerated or frozen compositions. In another embodiment, the MCTs are pre-blended with the other components to provide the beneficial amounts needed. In yet other embodiments, the MCTs are used to coat a food, snack, pet food composition, or pet treat. In one embodiment, the MCTs can be added to the composition just prior to offering it to the animal, e.g., using a sprinkled powder or a mix. Such compositions can further comprise other ingredients as discussed herein.

The compositions can optionally comprise one or more supplementary substances that promote or sustain general health. Such substances may be associated with improved mental health or enhanced cognitive function or may be substances that inhibit, delay, or decrease loss of cognitive function, e.g., herbs or plants that enhance cognitive function.

In various embodiments, pet food or pet treat compositions comprise from about 15% to about 50% crude protein. The crude protein material may comprise vegetable proteins such as soybean meal, soy protein concentrate, corn gluten meal, wheat gluten, cottonseed, and peanut meal, or animal proteins such as casein, whey, albumin, and meat protein. Examples of meat protein useful herein include pork, lamb, equine, poultry, fish, and mixtures thereof. Additionally, in one aspect, the compositions can include any protein source used or known to be utilized for hypoallergenic purposes, including hydrolyzed protein sources.

The compositions may further comprise from about 5% to about 40% fat. The compositions may further comprise a source of carbohydrate. The compositions may comprise from about 15% to about 60% carbohydrate. Examples of such carbohydrates include grains or cereals such as rice, corn, milo, sorghum, alfalfa, barley, soybeans, canola, oats, wheat, and mixtures thereof. The compositions may also optionally comprise other materials such as dried whey and other dairy by-products.

In some embodiments, the ash content of the composition ranges from less than 1% to about 15%, and in one aspect, from about 5% to about 10%.

The moisture content can vary depending on the nature of the composition. In one embodiment, the composition can be a complete and nutritionally balanced pet food. In another embodiment, the composition can be a hypoallergenic composition. In this embodiment, the pet food may be a "wet food", "dry food", or food of intermediate moisture content. "Wet food" describes pet food that is typically sold in cans or foil bags, and has a moisture content typically in the range of about 70% to about 90%. "Dry food" describes pet food which is of a similar composition to wet food, but contains a limited moisture content, typically in the range of about 5% to about 15% or 20%, and therefore is presented, for example, as small biscuit-like kibbles. In one embodiment, the compositions can have moisture content from about 5% to about 20%. Dry food products include a variety of foods of various moisture contents, such that they are relatively shelf-stable and resistant to microbial or fungal deterioration or contamination. Also included are dry food compositions which are extruded food products, such as pet foods, or snack foods for either humans or companion animals.

The compositions may also comprise one or more fiber sources. The term "fiber" includes all sources of "bulk" in the food whether digestible or indigestible, soluble or insoluble, fermentable or nonfermentable. Fibers can be from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, *psyllium*, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefit provided by the present invention to the immune system of an animal.

In other embodiments, the compositions can further comprise prebiotics or probiotics. Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as pet foods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of bifidobacteria in the colon, increasing calcium absorption, increasing fecal weight, shortening of gastrointestinal transit time, and possibly lowering blood lipid levels. The increase in bifidobacteria has been assumed to benefit human health by producing compounds to inhibit potential pathogens, by reducing blood ammonia levels, and by producing vitamins and digestive enzymes. Probiotic bacteria such as Lactobacilli or Bifidobacteria are believed to positively affect the immune response by improving the intestinal microbial balance leading to enhanced antibody production and phagocytic (devouring or killing) activity of white blood cells. *Bifidobacterium lactis* could be an effective probiotic dietary supplement for enhancing some aspects of cellular immunity in the elderly. Probiotics enhance systemic cellular immune responses and may be useful as a dietary supplement to boost natural immunity in otherwise healthy adults. Probiotics include many types of bacteria but generally are selected from four genera of bacteria: *Lactobacilllus acidophillus, Bifidobacteria, Lactococcus*, and *Pediococcus*. Beneficial species include *Enterococcus* and *Saccharomyces* species. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, and in one aspect, from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5% to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package.

The compositions and dietary supplements may be specially formulated for the intended recipients or consumers, such as for adult animals or for older or young animals. For example, a composition adapted for puppies or kittens or adapted for active, pregnant, lactating, or aging animals can be prepared. In general, specialized compositions will comprise energy and nutritional requirements appropriate for animals at different stages of development or age.

Certain aspects of the invention can be used in combination with a complete and balanced food. According to certain embodiments provided herein, the compositions comprising the MCTs can be used with a high-quality commercial food. As used herein, "high-quality commercial food" refers to a diet manufactured to produce the digestibility of the key nutrients of 80% or more, as set forth in, for example, the recommendations of the National Research Council above for dogs, or in the guidelines set forth by the Association of American Feed Control Officials. Similar high nutrient standards would be used for other animals.

In one embodiment, the food compositions comprise any of a variety of ingredients or combinations thereof selected for their contributions to the overall composition. Thus a skilled food technologist may choose from among natural (e.g., plant or plant-derived, animal or animal-derived, and microbial or microbially-derived), and synthetic ingredients or components. In particular embodiments, the ingredients may include any of the cereal grains and/or fractions or components thereof, meat and meat by-products, fish, shellfish, or other seafood, other animal products or by-products, eggs from any source, vitamins, minerals, salts, sweeteners, fiber, flavoring or other palatants, coloring, and functional ingredients such as emulsifiers, stabilizers, softeners, functional coatings, and the like. Cereals useful in the invention include all plants recognized as "cereal" crops, whether currently used in commercial agriculture or merely known practically or botanically as being a "cereal". For example, "cereals" includes corn, wheat, rice, barley, sorghum, millet, oats, rye, triticale, buckwheat, fonio, and quinoa. The skilled artisan will appreciate that in a given food composition, it is not uncommon to use one or more such cereal products. Meats useful in the invention include products from any animal, in one aspect, muscle tissue such as chicken or other poultry, lamb, sheep, veal, beef, or pork. Other animal products and by-products useful in the invention include dairy products or by-products derived from the milk of any species. Other important components or ingredients include fats and the skilled artisan will appreciate that many sources of vegetable, animal, or microbial fats are available for formulating food compositions. In one embodiment, the source of fat can be a plant fat such as corn, soy, or canola oil. In another embodiment, an animal fat, such as tallow, can be useful for providing calories from fat, as well as enticing flavor to meat-eating animals. Of course, combinations of any of the foregoing ingredients, such as fats, are known in the art and useful for optimizing the food compositions based on functional properties as well as price and availability.

The skilled artisan will also appreciate that in formulating the food compositions of the invention, the formulation may vary slightly, so as to allow consideration by the formulator of the price and/or availability of certain ingredients in the compositions, as well as the batch-to-batch variation in the analysis of certain ingredients. Thus a given food composition or formulation may vary slightly from batch to batch, plant to plant, or even season to season depending on such factors. Notwithstanding such variation in specific ingredients selected for manufacturing a particular batch of a food composition, the overall composition (for example, analysis of protein, carbohydrate, fat, fiber, or other component) may be held constant or at least substantially constant, for example, in accordance with a label claim, such as a claim or guarantee of a minimum or maximum percent of a particular component.

The skilled artisan will understand how to determine the appropriate amount of MCTs, and any other ingredients to be added to a given composition. The skilled formulator may consider important the animal's species, age, size, weight, health, and the like in determining how best to formulate a particular composition, food, or pharmaceutical composition comprising the MCTs and other components. Other factors that may be taken into account for formulation include the type of composition (e.g., pet food composition versus dietary supplement), the desired dosage of each component (MCTs), the average consumption of specific types of compositions by different animals (e.g., based on species, body weight, activity/energy demands, and the like) and the manufacturing conditions under which the composition is prepared. In one embodiment, the concentrations of MCTs and other ingredients to be added to the composition are calculated on the basis of the energy and nutrient requirements of the animal. When formulating the compositions of the present invention, a skilled can determine the amounts of the MCTs and other components of the compositions and of other compounds or ingredients, in for example a food composition, based upon the desired dosages and the characteristics of the animal.

For pet foods and food products formulated for human consumption, the amount of LCPUFA as a percentage of the composition can be in the range of about 0.1% to about 13% of the composition, although a greater percentage can be supplied. In various embodiments, the amount of LCPUFA can be about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, or more, e.g., 6%, 7%, 8%, 9%, 10%, 11%, 12%, 13%, 14%, 15%, 16%, 17%, 18%, 19%, 20% or more, of the composition. Up to 30, 40, or LCPUFA may be used in certain embodiments.

For pet foods and food products formulated for human consumption, the amount of NORC as a percentage of the composition can be in the range of about 0.1% to about 12% of the composition, although a greater percentage can be supplied. In various embodiments, the amount of NORC can be about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, or more, e.g., 6%, 7%, 8%, 9%, 10%, 11%, 12% or more, up to about 15% or even 20% of the composition. Dietary supplements may be formulated to contain several-fold higher concentrations of LCPUFA and NORC, to be amenable for administration to an animal in the form of a tablet, capsule, liquid concentrate, emulsion, suspension, gel, or other dosage form, or to be diluted before administration, such as by dilution in water, or adding to a pet food (for example, by spraying or sprinkling thereon), and other modes of administration suitable for administering such dietary supplements.

In one embodiment, the amount of MCT or AED in the composition can be a function of an amount required to establish specified concentrations, or a desired range of concentrations, of MCT and/or AED, or a metabolite thereof, in the blood serum of the animal. The specified concentrations, or desired ranges of MCT and/or AED in the blood serum may be calculated by determining the blood serum levels of animals fed the recommended amounts of MCT and/or AED specified above, as would be appreciated by one of skill in the art.

In one embodiment, the food compositions comprise a macronutrient composition suitable for the type of food being designed. In one aspect, the food composition has about 20 to 32% protein, about 30 to 50% carbohydrate, about 5% to 20% fat, and about 15% to 25% moisture. In another embodiment, the food composition can be a pet food composition such as a premium or super-premium pet food composition. In one embodiment, the pet food cam be formulated for canines and has a protein content of about 20-30%, about 24-28%, or even about 25-27%. In one embodiment, the protein content of a dog food composition can be about 26% by weight. In another embodiment, the formulation can be for felines and has a protein content of about 35-45%, 37-42%, or even about 39-41%. In one embodiment, the protein content of a cat food composition can be about 40%. In another embodiment, the composition can be a food product comprising MCTs, and further comprising about 15% to about 50% protein, about 5% to about 40% fat, about 5% to about 10% ash content, and having a moisture content of about 5% to about 20%.

In one embodiment, the food composition can be a wet food, such as a canned food, frozen food, or fresh food product. In another embodiment, the food composition can be shelf stable. In another, it must be refrigerated. In other embodiments, the food composition can be an intermediate moisture product or a dry food product as described above.

In one embodiment, the LCPUFA can be a fish oil and the NORC can be arginine or a nitric oxide-releasing derivative thereof. In certain embodiments, the compositions can comprise from about 0.1% to about 50% fish oil and from about 0.1% to about 20% arginine.

In one embodiment, the LCPUFA comprises one or more of a natural fish oil, ALA, EPA, DPA, DHA, or another n-3 fatty acid from any source. Combinations of LCPUFA sources are of course contemplated for use herein. LCPUFA with n-3 or n-6 are also contemplated for use in various embodiments.

In one embodiment, the composition can be formulated for a companion animal, e.g., a dog or cat. In other embodiments, the animal can be a human.

In other embodiments, the pharmaceutical compositions can comprise one or more pharmaceutically-acceptable carriers, diluents, or excipients. Generally, pharmaceutical compositions can be prepared by admixing a compound or composition with excipients, buffers, binders, plasticizers, colorants, diluents, compressing agents, lubricants, flavorants, moistening agents, and the like, including other ingredients known to skilled artisans to be useful for producing pharmaceuticals and formulating compositions that are suitable for administration to an animal as pharmaceuticals. Optionally, the pharmaceutical compositions further comprise MCTs, LCPUFAs, NORCs, B vitamins, and antioxidants.

In another aspect, the invention provides methods for treating epilepsy by administering the compositions described herein in an effect amount for treating epilepsy.

In some embodiments, the LCPUFA, MCTs, NORCs, B vitamins, and antioxidants can be administered to the animal in amounts given herein when describing the compositions. In certain embodiments, the daily dose for the compositions ranges from about 5 mg/day to about 5,000 mg/day, 10,000 mg/day, or 20,000 mg/day, or more per animal. In one aspect, the daily dose can range from about 30 mg/day to about 10,000 mg/day per animal, and in one aspect, from about 750 mg/day to about 7,500 mg/day per animal. The daily dose of LCPUFA, NORC, and MCTs can be measured in terms of grams of LCPUFA, NORC, and MCTs per kg of body weight (BW) of the animal. The daily dose of LCPUFA, NORC, and MCTs thereof can range from about 0.001 g/kg to about 50 g/kg BW of the animal, although greater or lesser doses can be provided. In one embodiment, the daily dose of LCPUFA, NORC, and MCTs can be from about 0.001 g/kg to about 25 g/kg BW of the animal. In one aspect, the daily dose of LCPUFA, NORC, and MCTs thereof can be from about 0.001 g/kg to about 10 g/kg BW of the animal. In another aspect, the daily dose of LCPUFA, NORC, and MCTs can be from about 0.001 g/kg to about 5 g/kg BW of the animal. In still another aspects, the daily dose of LCPUFA, NORC, and MCTs can be from about 0.001 g/kg to about 1 g/kg BW of the animal, or from about 0.001 g/kg to about 0.5 g/kg BW of the animal.

Administration in accordance with the methods can be on an as-needed or as-desired basis of varying or regular frequency. A goal of regular ingestion is to provide the animal with a regular and consistent dose of the composition or the direct or indirect metabolites that result from such ingestion. Such regular and consistent dosing will tend to create constant blood levels of the components of the compositions or their direct or indirect metabolites. Thus, regular administration can be once monthly, once weekly, once daily, or more than once daily. Similarly, administration can be every other day, week, or month, every third day, week, or month, every fourth day, week, or month, and the like. Administration can be multiple times per day. When utilized as a supplement to ordinary dietetic requirements, the composition may be administered directly to the animal, e.g., orally, or otherwise. The compositions can alternatively be contacted with, or admixed with, daily feed or food, including a fluid, such as drinking water, or an intravenous connection for an animal that is receiving such treatment. When utilized as a daily feed or food, administration will be well known to those of ordinary skill.

According to the methods of the invention, administration of the compositions, including administration as part of a dietary regimen, can span a period of time ranging from parturition through the adult life of the animal. In various embodiments, the animal can be a human or companion animal such as a dog or cat. In certain embodiments, the animal can be a young or growing animal. In other embodiments, the animal can be an aging animal. In some embodiments administration begins, for example, on a regular or extended regular basis, when the animal has exhibited signs of seizure or has been otherwise diagnosed with epilepsy.

Generally, the compositions can be administered to the animal in conjunction with one or more AEDs in an effective amount for treating epilepsy. In a specific embodiment, the composition administered can be the pharmaceutical composition that includes the AED and the MCT. In one embodiment, the composition can be administered to the animal on a daily basis in a single dose.

In a further aspect, the invention provides kits suitable for administering a composition comprising MCTs to an animal. The kits comprise in separate containers in a single package or in separate containers in a virtual package, as appropriate for the kit component, one or more MCTs and one or more of (1) one or more other ingredients suitable for consumption by an animal; (2) one or more AEDs; (3) instructions for how to combine or prepare the MCTs and any other ingredients provided in the kit for administration to an animal; (4) instructions for how to use the combined kit components, prepared kit components, or other kit components for the benefit of an animal; and (5) a device for administering the combined or prepared kit components to an animal. The components are each provided in separate containers in a single package or in mixtures of various components in different packages. The kits may comprise the ingredients in various combinations. For example, the kit could comprise a mixture of one or more MCTs and one or more food ingredients in one container and one or more other ingredients in one or more other containers. Similarly, the kit could comprise a single food composition containing the MCTs with an additional compartment for an AED. Other such combinations can be produced by the skilled artisan based upon the characteristics of the ingredients and their physical and chemical properties and compatibilities.

In another aspect, the invention provides a means for communicating information about or instructions for one or more of (1) using compositions of the present invention for treatment of epilepsy; (2) admixing the MCTs, or other components of the invention to produce a composition suitable for treatment of epilepsy; (3) using the kits of the present invention for treatment of epilepsy; and (4) administering the compositions to an animal. The means comprises one or more of a physical or electronic document, digital storage media, optical storage media, audio presentation, audiovisual display, or visual display containing the information or instructions. In one embodiment, the means can be selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, the invention provides methods for manufacturing a food composition comprising MCTs and one or more other ingredients suitable for consumption by an animal, e.g., protein, fat, carbohydrate, fiber, LCPUFAs, NORCs, B vitamins, and antioxidants. The methods comprise admixing one or more ingredients suitable for consumption by an animal with MCTs, and possibly other ingredients. Alternatively, the methods comprise applying MCTs, and other ingredients if desired, separately or in any combination onto the food composition, e.g., as a coating or topping. The MCTs can be added at any time during the manufacture and/or processing of the food composition. This includes, for example, admixing the MCTs as part of the core formulation of the "body" of the food composition or applying them as a coating, i.e., primarily to the surface of the food composition after its manufacture. The compositions can be made according to any method suitable in the art.

In another aspect, the present invention provides a package comprising a composition of the present invention and a label affixed to the package containing a word or words, picture, design, acronym, slogan, phrase, or other device, or combination thereof, that indicates that the contents of the package contains a composition suitable for treatment of epilepsy in an animal. Typically, such device comprises the words "treats epilepsy", "improves epilepsy treatment", "enhances epileptic treatment", or an equivalent expression printed on the package. Any package or packaging material suitable for containing the composition is useful in the invention, e.g., a bag, box, bottle, can, pouch, and the like manufactured from paper, plastic, foil, metal, and the like. In one embodiment, the package contains a food composition adapted for a particular animal such as a human, canine or feline, as appropriate for the label, in one aspect, a companion animal food composition.

The pharmaceutical compositions of the invention can be administered to the animal using a variety of administration routes. Such routes include oral, intranasal, intravenous, intramuscular, intragastric, transpyloric, subcutaneous, rectal, and the like. In one embodiment, the compositions can be administered orally.

EXAMPLES

The invention can be further illustrated by the following example, although it will be understood that this example is included merely for purposes of illustration and is not intended to limit the scope of the invention unless otherwise specifically indicated.

Example 1

Epilepsy Study for Canines

A 6-month prospective, randomized, double blinded, placebo controlled, crossover dietary trial comparing an MCT-containing diet to a standardized placebo diet containing no MCTs in canine epilepsy was performed. Subjects were fed either the MCT or placebo diet for 3 months (Day 1 to Day 90±2 days) followed by a subsequent respective switch of diet for a further 3 months (Day 90 to Day 180±2 days). Relevant data were collected on the following variables at visit 1 (Day -2), visit 2 (Day 90±2 days) and visit 3 (day 180±2 days): seizure frequency; body weight; measurements of serum phenobarbital (PB) and/or (potassium bromide) KBr concentration as appropriate; dynamic bile acids; complete blood cell count; standard clinical serum chemistry; and adverse events. The diet allocations were randomized and only available to the study nurse who was also the diet dispenser, hence owners, investigators and statisticians involved were blinded throughout the study.

Subjects were recruited on the basis of the following exclusion and inclusion criteria that were verified by telephone interviews followed by physical and laboratory examinations: canine species of mixed or purebred breeds; suspected to have idiopathic epilepsy (unremarkable former magnetic resonance imaging (MRI) scan and cerebrospinal fluid (CSF) analysis); age between 6 months and less than or equal to 12 years; weight between 4 kg and less than or equal to 65 kg; no clinically significant findings on haematology and biochemistry or dynamic bile acid results; have unremarkable interictal neurological examinations for a dog on antiepileptic treatment; only one dog per household enrolled on study; have at least 3 seizures in previous 3 months prior to start of study; on at least one antiepileptic treatment; no use of drugs that could influence the metabolism of PB and KBr. Dogs intended for breeding in less than two weeks from start of study; with known cause of epilepsy such as brain neoplasm, brain trauma, encephalitis and meningitis; with chronic or acute renal, hepatic or cardiac failure; with an acute or surgical condition at the time of enrolment and bitches known or suspected to be pregnant or lactating were all excluded from the study.

The MCT diet was the commercially available ProPlan® Senior 7+Chicken and Rice formula manufactured in France and formulated to contain 5.6% MCTs, at least 26% crude protein, at least 15% crude fat, and 50% carbohydrates with less than 2% as crude fiber. The placebo formula is of similar composition, with the exception that zero MCTs were added, and lard was used as fat substitute to ensure that the formulas were isocaloric. The dogs were housed and fed mainly once daily at home and there were no restrictions on water consumption. The owners were educated to keep diet consistent throughout the study period.

Seizure frequency refers to the number of seizures per month and seizure-days refers to the number of days in a month with seizure occurrence. The severity of seizures was analyzing using the McNemar test by comparing the presence of cluster seizures between diet groups. Comparisons made between the MCT and placebo standardized diet groups were made using match-paired student's t tests for parametric data and Wilcoxon matched-pairs signed rank test for non-parametric data where both were used two-sided and $P<0.05$ was considered significant. Non-parametric data are presented as median (25-75% percentile) and parametric data are shown as mean (+/−SD).

The present study used twenty-one dogs of 17 different canine breeds including: American bulldog; 2 Beagles; 2 Border Collies; Boxer; Cavalier King Charles Spaniel; English Bull Terrier; English Springer Spaniel; German Shepherd; Golden Retriever; Lhasa Apso; Mastiff; Rhodesian Ridgeback; Saint Bernard; Siberian Husky; Slovakian Rough Haired Pointer; Welsh Springer Spaniel and 3 Cross breeds. The study population consisted of 15 males, of which 10 were neutered and 5 were intact and 6 females of which 4 were neutered and 2 were intact. The dogs were of 4.59±1.73 years of age and weighed 29.79±14.73 kilograms at start of trial. All 21 dogs received PB. Most dogs were also treated additionally with KBr (n=18). Some dogs were chronically treated with a third AED, imepitoin (n=1) or levetiracetam (n=4). Twelve owners had rectal diazepam or levetiracetam for pulse therapy at home available for the acute treatment of cluster seizure episodes. There was no difference for the acute or chronic treatment regimens between the placebo or MCT phase.

Effects on Seizure Frequency, Seizure Days and Severity of Seizures

The results revealed a significantly lower seizure frequency when dogs were on the MCT (2.8/month, 0-10/month) in comparison to the placebo diet (4.4/month, 0.3-22.9/month, p=0.0195; Table 1). Three dogs achieved complete seizure freedom (100% reduction), 7 dogs had a 50% or greater reduction in seizure frequency (56.85%, 50.76-62.8%) and 5 dogs had an overall reduction in seizure frequency (38.87%, 35.68-43.27%). Six dogs showed no response to the MCT with an overall increase in seizure frequency.

TABLE 1

| CASE ID | Placebo diet Seizure frequency/ month | MCT diet Seizure frequency/ month | change |
|---|---|---|---|
| RVE02 | 1.7 | 1.0 | −39.3% |
| RVE05 | 4.4 | 8.0 | 80.5% |
| RVE06 | 11.6 | 5.7 | −51.2% |
| RVE09 | 1.9 | 1.0 | −47.2% |
| RVE12 | 0.3 | 1.7 | 388.9% |
| RVE13 | 1.3 | 2.3 | 73.1% |
| RVE14 | 3.5 | 2.3 | −33.5% |
| RVE15 | 2.0 | 0.0 | −100.0% |
| RVE16 | 2.0 | 2.3 | 12.9% |
| RVE17 | 22.9 | 9.9 | −56.9% |
| RVE19 | 3.7 | 2.3 | −37.8% |
| RVE20 | 2.7 | 1.3 | −50.0% |
| RVE21 | 10.6 | 5.2 | −50.8% |
| RVE22 | 3.6 | 3.9 | 7.9% |
| RVE23 | 6.1 | 2.3 | −61.5% |
| RVE25 | 2.6 | 1.0 | −62.1% |
| RVE27 | 5.4 | 3.3 | −38.9% |
| RVE28 | 2.3 | 0.7 | −71.1% |
| RVE29 | 0.7 | 0.0 | −100.0% |
| RVE30 | 3.4 | 5.0 | 48.3% |
| RVE33 | 0.3 | 0.0 | −100.0% |

Seizure days were also shown to be significantly lower when dogs were on the MCT in comparison to the placebo diet (p=0.0216) with over 76% of the trial population achieving reduction in seizure days (Table 2). During the MCT treatment, 3 dogs achieved complete seizure freedom (100% reduction), 5 dogs had over 50% reduction in seizure days (67.14%, 58.22-75.14%), and 8 dogs had less than 50% reduction in seizure days (29.68%, 6.839-41.22%). five dogs showed no response to the MCT with an overall increase in number of seizure days.

TABLE 2

| CASE ID | PLACEBO Seizure DAYS | TEST Seizure DAYS | change |
|---|---|---|---|
| RVE02 | 5 | 2 | −60.0% |
| RVE05 | 7 | 12 | 71.4% |
| RVE06 | 5 | 6 | 20.0% |
| RVE09 | 5 | 2 | −60.0% |
| RVE12 | 1 | 6 | 500.0% |
| RVE13 | 3 | 7 | 133.3% |
| RVE14 | 11 | 7 | −36.4% |
| RVE15 | 5 | 0 | −100.0% |
| RVE16 | 3 | 3 | 0.0% |
| RVE17 | 41 | 23 | −43.9% |
| RVE19 | 10 | 6 | −40.0% |
| RVE20 | 5 | 4 | −20.0% |
| RVE21 | 22 | 16 | −27.3% |
| RVE22 | 6 | 5 | −16.7% |
| RVE23 | 12 | 3 | −75.0% |
| RVE25 | 6 | 3 | −50.0% |
| RVE27 | 12 | 7 | −41.7% |
| RVE28 | 4 | 1 | −75.0% |
| RVE29 | 2 | 0 | −100.0% |
| RVE30 | 8 | 6 | −25.0% |
| RVE33 | 1 | 0 | −100.0% |

The MCT diet resulted in a shift in the distribution of seizure frequencies per month with higher percentages of the whole population (n=21) experiencing reduced seizure frequencies compared to the placebo standardized diet. The total number of seizures that occurred in the study population (n=21) on each day of the MCT period was also reduced in comparison to the placebo diet (Table 3). The results also show a reduction in the number of subjects with seizure occurrences during the MCT period with a stable distribution of around 3 subjects with seizure occurrences per day. On the other hand, during the standardized placebo diet the distribution was more varied with higher number of subjects with seizure occurrences per day. There were no significant differences in the number of days with cluster seizures between diet groups (p=0.6171).

TABLE 3

| CASE ID | Total seizures with placebo diet | Total seizures with MCT diet | change |
|---|---|---|---|
| RVE02 | 5 | 3 | −40.0% |
| RVE05 | 13 | 24 | 84.6% |
| RVE06 | 36 | 17 | −52.8% |
| RVE09 | 6 | 3 | −50.0% |
| RVE12 | 1 | 6 | 500.0% |
| RVE13 | 4 | 7 | 75.0% |
| RVE14 | 11 | 7 | −36.4% |
| RVE15 | 6 | 0 | −100.0% |
| RVE16 | 6 | 7 | 16.7% |
| RVE17 | 68 | 30 | −55.9% |
| RVE19 | 12 | 7 | −41.7% |
| RVE20 | 8 | 4 | −50.0% |
| RVE21 | 31 | 17 | −45.2% |
| RVE22 | 11 | 12 | 9.1% |
| RVE23 | 18 | 7 | −61.1% |
| RVE25 | 8 | 3 | −62.5% |
| RVE27 | 16 | 10 | −37.5% |
| RVE28 | 7 | 2 | −71.4% |
| RVE29 | 2 | 0 | −100.0% |
| RVE30 | 10 | 15 | 50.0% |
| RVE33 | 1 | 0 | −100.0% |

Effect on Body Weight, Serum AED Concentration, Complete Blood Count and Clinical Chemistry There were no significant changes in serum concentrations of PB (26.50 µg/ml, 23.50-34.00 µg/ml v. 32.50 µg/ml, 25.00-36.75 µg/ml, p=0.4233) and potassium bromide (1.23 mg/ml, 1.09-1.89 mg/ml v. 1.29 mg/ml, 1.02-1.61 mg/ml, p=0.4037) or weight (29.79, ±15.16 kg v. 29.61, ±15.51 kg, p=0.2997) between the placebo-standardized diet and MCT respectively. Complete blood count and clinical chemistry results, including glucose, were not significantly different between diet groups.

In the specification, there have been disclosed typical embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims the invention may be practiced otherwise than as specifically described.

What is claimed is:

1. A method for enhancing the effect of an anti-epileptic drug (AED) in an animal comprising administering a food composition comprising a medium chain triglyceride (MCT) and a nitric oxide releasing compound in conjunction with an anti-epileptic drug (AED) to the animal, wherein the MCT is of Formula 1:

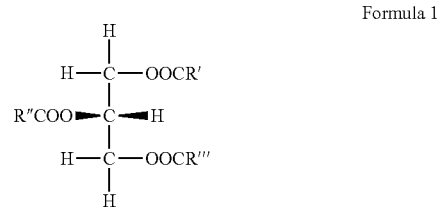

Formula 1 wherein the R', R", and R''' esterified to the glycerol backbone are each independent fatty acids having 5-12 carbons; wherein the MCT is administered in an effective amount for enhancing the effect of the AED in the animal.

2. The method of claim 1, wherein the animal is a companion animal.

3. The method of claim 1, wherein the animal is a canine or a feline.

4. The method of claim 1, wherein the AED is selected from the group consisting of acetazolamide, carbamazepine, chlorazepate, clobazam, clonazepam, diazepam, eslicarbazepine acetate, ethisyxunudem, ethosuximide, felbamate, gabapentin, imepitoin, keppra, lacosamide, lamotrigine, levetiracetam, methylphenobarbitone, nitrazepam, oxcarbazepine, perampanel, piracetam, phenobarbital, phenytoin, potassium bromide, pregabalin, primidone, retigabine, rufinamide, sodium bromide, sodium valproate, stiripentol, sulthiame, tiagabine, topiramate, valporic acid, vigabatrin, zonisamide, salts thereof, and mixtures thereof.

5. The method of claim 1, wherein the food composition comprises from about 1% to about 15% of the MCT and the food composition is administered simultaneously with the AED.

6. The method of claim 1, wherein the food composition is administered on an extended regular basis.

7. The method of claim 1, wherein the food composition is administered to the animal on a daily basis.

8. The method of claim 1, wherein the administration results in a reduction in seizure frequency of the animal by at least 50% compared to administration of the AED with a food composition not containing the MCT.

\* \* \* \* \*